Figure 1:
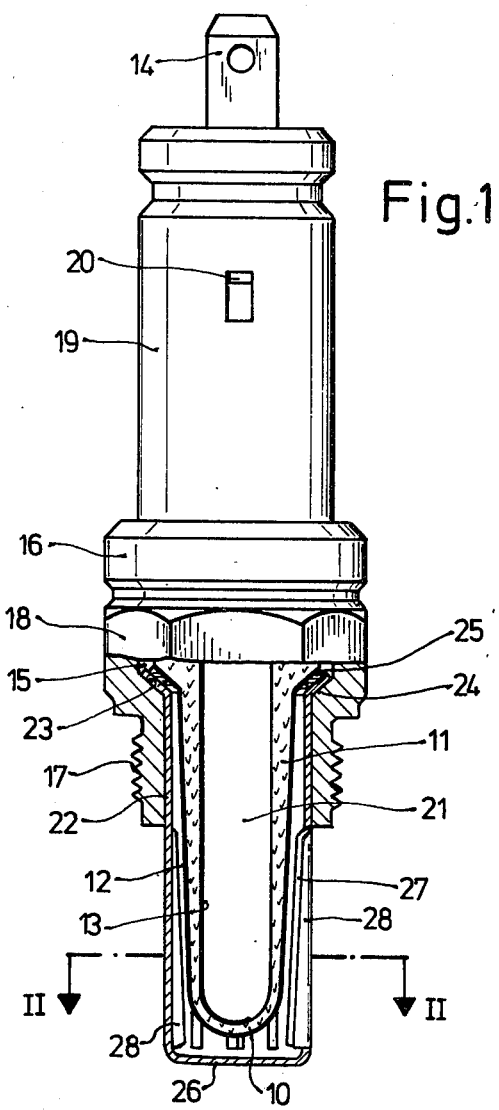

United States Patent [19]

Hacker et al.

[11] 4,065,372
[45] Dec. 27, 1977

[54] ELECTROCHEMICAL OXYGEN SENSING ELEMENT, PARTICULARLY FOR DETERMINATION OF OXYGEN CONTENT IN THE EXHAUST GASES OF AUTOMOTIVE INTERNAL COMBUSTION ENGINES

[75] Inventors: Wolf-Dieter Hacker, Asperg; Karl-Hermann Friese, Leonberg; Leo Steinke, Waiblingen-Hegnach; Helmut Weyl, Schwieberdingen, all of Germany

[73] Assignee: Robert Bosch GmbH, Stuttgart, Germany

[21] Appl. No.: 736,253

[22] Filed: Oct. 27, 1976

[30] Foreign Application Priority Data

Nov. 27, 1975 Germany .............................. 2553292

[51] Int. Cl.² ........................................... G01N 27/46
[52] U.S. Cl. ................................................ 204/195 S
[58] Field of Search ............. 204/1 S, 195 S; 60/276, 60/285, 289; 123/119 E; 324/29, 71 R

[56] References Cited

U.S. PATENT DOCUMENTS

| 3,844,920 | 10/1974 | Burgett et al. ................. 204/195 S |
| 3,891,529 | 6/1975 | Beesch .............................. 204/195 S |
| 3,960,692 | 6/1976 | Weyl et al. ....................... 204/195 S |
| 3,960,693 | 6/1976 | Weyl et al. ....................... 204/195 S |

Primary Examiner—G. L. Kaplan
Attorney, Agent, or Firm—Flynn & Frishauf

[57] ABSTRACT

To provide protection to the sensitive solid ion conductive electrolyte, a metal sleeve is placed to surround the electrolyte, with clearance, and formed with openings having an increasing cross-sectional area starting from the housing or socket towards the bottom of the solid electrolyte tube to provide an approximately even temperature gradient upon exposure of the element to exhaust gases, the sleeve being additionally so formed that deflection surfaces or vanes are formed internally thereof, for example by punching the openings through the sleeve as elongated slots leaving deflecting vanes, to deflect gases passing through the openings from direct impingement on the solid electrolyte tube to protect the solid electrolyte tube against impact and contamination.

11 Claims, 2 Drawing Figures

U.S. Patent  Dec. 27, 1977  4,065,372

4,065,372

ELECTROCHEMICAL OXYGEN SENSING ELEMENT, PARTICULARLY FOR DETERMINATION OF OXYGEN CONTENT IN THE EXHAUST GASES OF AUTOMOTIVE INTERNAL COMBUSTION ENGINES

CROSS REFERENCE TO RELATED APPLICATIONS AND PATENTS

U.S. Pat. No. 3,841,987, FRIESE et al; U.S. Pat. No. 3,978,006, TOPP et al; U.S. Ser. No. 643,934, filed Dec. 23, 1975, WEYL et al now U.S. Pat. No. 4,019,914; U.S. Ser. No. 447,475, filed Mar. 4, 1974, POLLNER et al now U.S. Pat. No. 4,021,326; all assigned to the assignee of the present application.

The present invention relates to an electrochemical oxygen sensing element, and more particularly to such an element to sense the oxygen content of exhaust gases of internal combustion engines, especially automotive-type internal combustion engines, by exposing a solid ion conductive electrolyte tube to the exhaust gases to thereby sense oxygen concentration in the exhaust gases.

It has previously been proposed — see the cross-referenced patents — to expose a solid ion conductive electrolyte tube to the exhaust gases of internal combustion engines; the tube is closed at one end and uses oxygen in ambient air as a reference by exposing the inside of the closed tube to ambient air, the outside of the tube being exposed to the exhaust gases. The inside of the tube has an electron conductive path connected thereto which, in turn, is connected to a terminal. The outside of the tube is formed with an electron conductive catalyzing layer which is connected to a terminal, e.g. the metallic socket and hence to ground or chassis of the installation with which the sensor is associated.

The solid ion conductive electrolyte is a tube which is mechanically sensitive and fragile, and thus must be protected. It has previously been proposed to protect the tube by providing a protective outer sleeve which is formed with openings and so arranged that gases are deflected upon penetrating the openings so they do not directly impinge on the solid electrolyte tube.

Electrochemical sensors of this type in which a perforated protective sleeve is provided still are subject to damage; the electron conductive catalyzing layer at the outside of the solid electrolyte tube is damaged, and can be entirely destroyed when the exhaust gases from internal combustion engines, including coarse particles and contaminants therein, impinge on the catalyzing layer. The solid electrolyte tube behind the openings of the protective sleeves, and the catalyzing layer thereon, are additionally subjected to temperature shocks as well as pressure shocks upon sudden changes in temperature and pressure conditions of the exhaust gases. Perforated sleeve or mesh arrangements as proposed, while providing better protection than no such sleeve at all, still could not meet the rigorous requirements of long lifetime of the unit as a whole and effective protection over a long period of time.

It has previously been proposed to provide deflection elements associated with the perforations of protective sleeves which are so arranged that the penetrating gas and particles therein are prevented from direct impingement on the solid electrolyte tube. In one such arrangement, two concentric sleeves were used in which the axes of perforations are offset with respect to each other, the sleeves themselves being coaxially located with spacing from each other and from the solid electrolyte tube, respectively.

The arrangement using a plurality of concentric protective sleeves has been found quite efficient to prevent mechanical attack on the solid ion conductive electrolyte tube due to particles, pressure variations and the flow of exhaust gases; they also provide some protection with respect to temperature and pressure shocks, that is, sudden variations of the respective parameter. It is, however, desirable to still increase the lifetime of the unit as a whole.

It is an object of the present invention, to provide an electrochemical sensing element, and more particularly an oxygen sensor to sense the oxygen content of the exhaust gases of internal combustion engines, especially automotive-type internal combustion engines, which is essentially immune to mechanical attack and, further, can tolerate heat and pressure shocks arising in the exhaust gases, by isolating such heat and pressure shocks as well as mechanical attack due to the presence of the exhaust gases from the solid electrolyte tube of the sensor.

SUBJECT MATTER OF THE PRESENT INVENTION

It is believed that the reason for failure of sensor elements may be due to the high-temperature gradients which arise between the portion of the solid ion conductive electrolyte tube which is exposed to the exhaust gases themselves and those portions which are only indirectly contacted by the exhaust gases and which are close to the socket element of the sensor. These high-temperature gradients may result in actual temperture jumps along the length of the tube, the gradient being non-uniform along the length resulting in highly heated portions adjacent the portions of substantially cooler temperature.

In accordance with the present invention, a protective element or sleeve is provided, surrounding the solid ion conductive electrolyte of the sensor, and formed with openings and deflection elements which are so shaped that the cross section of the opening is greater towards the closed end exposed deepest to the exhaust gases when the sensor is introduced essentially transversely into the exhaust stream from an internal combustion engine, the openings decreasing in size towards the socket portion to ensure an essentially uniform temperature gradient along the length of the solid ion conductive tube upon exposure to a stream of exhaust gases. In accordance with a preferred feature of the invention, the openings in the protective sleeve are formed as longitudinal slits which increase in dimension, wedge-shaped, towards the far end of the sensor, that is, towards the closed bottom of the tube of solid ion conductive electrolyte material. The wedge-shaped openings can be punched from the sleeve and so shaped that internal vanes are provided which guide impinging gases in a circular path around the solid ion electrolyte material, preventing direct impingement.

Figure 2:
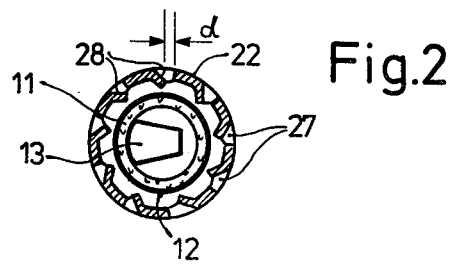

The invention will be described by way of example with reference to the accompanying drawings, wherein:

FIG. 1 is a side view, partly in section, of an electrochemical sensing element in accordance with the present invention, and drawn to an enlarged scale;

and FIG. 2 is a cross section along line II—II of FIG. 1.

The sensor illustrated in FIGS. 1 and 2 operates on the basis of a solid ion conductive electrolyte oxygen concentration sensor. It includes a solid ion conductive tube 11 closed off at its bottom 10, and made of stabilized cubic zirconium dioxide (see cross-referenced patents), the outside of which has an electron conductive catalyzing layer 12 of platinum applied thereto. The inside of the closed tube has an electron conductive path 13 applied, preferably as a strip of platinum, which extends into the region of the tube 10 of the sleeve 11. The conductive path 13 need not be platinum but preferably is a thin coating strip thereof. The conductive path 13 is connected electrically by suitable connection means to a terminal 14 extending from the socket portion 16. Socket portion 16 is a metallic housing formed with a longitudinal bore 15 in which the tube 11 is inserted and sealed thereto. The housing 16 is formed with a hexagonal engagement area 18, for engagement with a socket wrench, and is threaded, as seen at 17, for introduction into the exhaust stream from an internal combustion engine, for example by extending transversely to the direction of flow of the exhaust gases, being introduced, for example, at right angles through a portion of the exhaust system of an automotive internal combustion engine. An external protective tube 19 is connected to housing 16, for example by mechanical rolling or crimping into a groove. The tube 19 is formed with a reference air opening 20 to permit access to the interior space of the tube 11 of ambient air to provide a reference oxygen concentration to the interior of the closed solid electrolyte tube 11.

The end portion of the solid electrolyte tube 11, with its bottom 10 which is exposed to exhaust gases, extends from the longitudinal bore of the socket 15 and is exposed to exhaust gases from internal combustion engines. To protect the electron conductive catalyzing layer 12 and the solid electrolyte tube 11 against mechanical attack due to the flow of gases from the engine, particles, grains, and various solids therein, as well as against temperature and pressure shocks due to the impinging exhaust gas, a protective sleeve 22 is placed to surround the solid ion conductive electrolyte 11. The protective sleeve 22 is formed with a flange 23 which is seated in a shoulder 24 of the longitudinal bore 15 of the socket 16. It is seated by means of a soft metal ring 25 on the solid electrolyte tube 11. The protective sleeve 22 has a bottom 26. It surrounds the solid electrolyte tube 11, with clearance. The bottom 26 is not strictly necessary, but is preferred. The protective sleeve 22 is formed with openings 27 in the region thereof which extends from the socket 16 to permit exhaust gases to come in contact with the solid electrolyte tube 11.

In accordance with the present invention, the openings 27 are specifically shaped and formed. The openings 27 can be punched from the tube 22 and are shaped to leave deflection vanes 28 which direct the hot exhaust gases and solid particles contained therein away from direct impingement with the catalyzing layer 12 of the solid electrolyte tube 11, and the tube 11 itself, to prevent damage by impingement of the particles. In essence, the deflecting vanes 28, as best seen in FIG. 2, are so arranged that impinging gases are directed in a circular path around the solid electrolyte tube 11 so that the gases form eddies surrounding the tube 11 and its catalyzing layer 12. The deflecting vanes 28 additionally provide protection against temperature and pressure shock effects. The gases flow as in a spinning turbine, as described, providing protection against pressure and temperature effects for the tube 11 and the catalyzing layer 12. The openings 27, in accordance with the invention, are arranged to provide a greater cross section in the region of the bottom 10 of the tube 11 than at the socket end. In accordance with a feature of the invention, they are formed as wedge-shaped slits, the cross section of which decreases towards the end of the sleeve 22 adjacent the socket 16. The slit-shaped openings 27 terminate approximately in the region of the bottom 10; the bottom 26 of the sleeve 22 is left solid. The largest cross section of the slits 27 is in the region of the bottom 10 of the solid electrolyte tube.

The wedge-shaped slits 27 provide maximum exposure of the bottom 10 of the solid electrolyte tube 11 to exhaust gases; it is this region of the bottom 10 which forms the actual measuring zone of the sensor, and which, hence, has most extensive exposure to the exhaust gases. That portion of the solid electrolyte tube 11 which extends towards the socket 16 is still exposed to exhaust gases, however, to provide a temperature gradient which is essentially uniform and does not have jump-like sharp gradient regions. The temperature of the tube 11, therefore, decreases essentially uniformly along its length, and stresses due to temperature changes, non-uniformities in temperature gradients and particularly high temperature gradients and temperature jumps can be avoided. It has been found that the lifetime of such sensors, even over many cycling times of temperature variations is substantially increased.

Various changes and modifications may be made; for example, rather than forming the slits 27 to increase in cross-sectional area towards the bottom 10 of the solid electrolyte tube, a larger number of slits can be formed as the distance of the sleeve 22 from its end seated in socket 16 increases; and these additional slits may also be formed with varying opening size.

The sleeve 22 should be made of a heat-resistant material, for example: X 12 Cr Ni 25/21. The thickness of sleeve 22, of the aforementioned material, was: 0.4 mm; the length of the sleeve 22 from the end of the threaded portion 17 of socket 16, that is, the extending portion, was about 20 mm; the outer diameter of tube 11 was 8 mm, and the clearance between the normal circumference of tube 22 and tube 11 was 2 mm. At the tip end, the maximum size opening as defined by dimension $d$ (FIG. 2), was 0.8 mm, and there were 9 openings spaced around the circumference of the sleeve 22. A sensor of this construction would be suitable for use, for example, as an exhaust gas sensor in the exhaust system of an automotive-type internal combustion engine, when exposed to exhaust gases of temperatures up to about 950° C.

The solid electrolyte tube 11 may additionally be protected by a protective coating disclosed in cross-referenced application U.S. Ser. No. 447,475, filed Mar. 4, 1974, POLLNER et al, now U.S. Pat. No. 4,021,326 assigned to the assignee of the present application, and reference to the protection of the solid electrolyte tube herein is directed to the tube, as coated with various layers, as previously described, for example in the cross-referenced patents and applications.

We claim:

1. Electrochemical oxygen sensing element to determine the oxygen content in the exhaust gases from internal combustion engines having a housing (16, 17, 18, 19);

a solid electrolyte tube (11) having a first end closed at the bottom (10) and having an opposite end mounted in the housing and projecting therefrom, the solid electrolyte tube forming a solid ion conductive electrolyte oxygen concentration measuring element;

first electrode means (13) at the inside of the tube (11) extending into the region of the closed bottom thereof;

means (20) formed in the housing providing access of ambient air to the inside of the solid electrolyte tube (11) to establish an oxygen reference potential;

second electrode means (12) at the outside of the tube (11) and forming a catalyzing layer, connected to a terminal of said element;

and a protective tube (22) surrounding the solid electrolyte tube, with clearance, and secured in the housing formed with opening therein to expose the outside of the tube (11) with said catalyzing layer (12) to the exhaust gases;

wherein, in accordance with the invention, means are provided formed on the protective tube to establish a substantially uniform temperature gradient of the solid electrolyte tube, when said solid electrolyte tube is exposed to hot exhaust gases from the internal combustion engine including said openings (27) formed in the protective tube (22) having an increase in cross-sectional free area in the direction from the housing towards the bottom of the solid electrolyte tube, the largest open area of the openings (27) being approximately in the region of the closed region of the closed bottom (10) of the solid electrolyte tube (11) so that the area of said openings in the vicinity of the end of the tube in the housing has a smaller cross-section than the openings in the vicinity of the closed end.

2. Sensing element according to claim 1, wherein the openings (27) in the protective tube (22) are longitudinal slits of increasing open width.

3. Sensing element according to claim 1, wherein the protective tube (22) has a closed bottom (26).

4. Sensing element according to claim 3, wherein the openings are punched-out slits leaving internally projecting portions (28), said portions forming said deflection means, the portions being bent inwardly to a greater extent at the end adjacent the bottom (10) of the solid electrolyte tube to provide a greater clear opening cross section of the opening (27) formed by the punched-out projections;

and wherein the width of the openings formed by the punched-out internally projecting portions has a cross-sectional area distribution matched approximately to the temperature gradient arising in the solid electrolyte tube (11) when exposed to the exhaust gases of internal combustion engines.

5. Sensing element according to claim 4, wherein the punched-out projections (28) are bent inwardly to form directing flaps or directing vanes for gases passing through the openings and impinging on said punched-out flaps or vanes to direct gas flow in a circular path around the electrolyte tube (11).

6. Sensing element according to claim 1, wherein the openings are longitudinal, wedge-shaped slits (27) extending lengthwise of the protective tube (22).

7. Sensing element according to claim 1, wherein the openings are punched-out slits leaving internally projecting portions (28), said portions forming said deflection means, the portions being bent inwardly to a greater extent at the end adjacent the bottom (10) of the solid electrolyte tube to provide a greater clear opening cross section of the opening (27) formed by the punched-out projections.

8. Sensing element according to claim 7, wherein the punched-out projections (28) are bent inwardly to form directing flaps or directing vanes for gases passing through the openings and impinging on said punched-out flaps or vanes to direct gas flow in a circular path around the electrolyte tube (11).

9. Sensing element according to claim 1, wherein the cross-sectional area of the openings (27) is of gradually decreasing size distribution longitudinally with respect to the solid electrolyte tube from the bottom (10) thereof towards the housing, the size of the opening being matched approximately in accordance with the temperature gradient established during operation upon passage of hot combustion exhaust gases through said openings and arising in the solid electrolyte tube from the closed end to the end mounted in the housing to establish an essentially uniform temperature gradient from the solid bottom (10) of the solid electrolyte tube (11) towards the housing.

10. Sensing element according to claim 9 further comprising deflection means (28) formed on the protective tube (22) to deflect gases passing through the openings (27) therein from direct impingement on the solid electrolyte tube (11) to protect said solid electrolyte tube against impact by particles carried in the gases, by direct exposure to gas flow stream, and from contamination.

11. Sensing element according to claim 1 further comprising deflection means (28) formed on the protective tube (22) to deflect gases passing through the openings (27) therein from direct impingement on the solid electrolyte tube (11) to protect said solid electrolyte tube against impact by particles carried in the gases, by direct exposure to gas flow stream, and from contamination.

* * * * *